(12) United States Patent
Reed et al.

(10) Patent No.: US 9,125,704 B2
(45) Date of Patent: Sep. 8, 2015

(54) HAMMER TOE IMPLANT WITH EXPANSION PORTION FOR RETROGRADE APPROACH

(71) Applicant: Wright Medical Technology, Inc., Arlington, TN (US)

(72) Inventors: Wesley Reed, Memphis, TN (US); Dinesh V. Koka, Memphis, TN (US)

(73) Assignee: Wright Medical Technology, Inc., Memphis, TN (US)

( * ) Notice: Subject to any disclaimer, the term of this patent is extended or adjusted under 35 U.S.C. 154(b) by 109 days.

(21) Appl. No.: 14/071,322

(22) Filed: Nov. 4, 2013

(65) Prior Publication Data

US 2014/0058462 A1 Feb. 27, 2014

Related U.S. Application Data

(63) Continuation of application No. 13/099,691, filed on May 3, 2011, now Pat. No. 8,608,785.

(60) Provisional application No. 61/350,663, filed on Jun. 2, 2010, provisional application No. 61/434,491, filed on Jan. 20, 2011.

(51) Int. Cl.
| | |
|---|---|
| *A61B 17/88* | (2006.01) |
| *A61B 17/56* | (2006.01) |
| *A61B 17/84* | (2006.01) |
| *A61B 17/16* | (2006.01) |
| *A61B 17/72* | (2006.01) |
| *A61B 17/86* | (2006.01) |

(Continued)

(52) U.S. Cl.
CPC ............ *A61B 17/88* (2013.01); *A61B 17/1604* (2013.01); *A61B 17/1682* (2013.01); *A61B 17/56* (2013.01); *A61B 17/7266* (2013.01); *A61B 17/7291* (2013.01); *A61B 17/844* (2013.01); *A61B 17/862* (2013.01); *A61B 17/8883* (2013.01); *A61B 2017/0243* (2013.01); *A61B 2017/564* (2013.01); *A61B 2017/565* (2013.01); *A61F 2002/423* (2013.01)

(58) Field of Classification Search
CPC .......... A61B 17/1604; A61B 17/1682; A61B 17/56; A61B 2017/564; A61B 2017/565; A61B 17/7266; A61B 17/7291; A61B 17/862; A61B 17/844; A61B 17/88
USPC ......... 81/451–453; 411/388, 451.3, 456–457, 411/459, 487; 606/96, 99, 104, 300–301, 606/305, 307–309, 319, 326–327
See application file for complete search history.

(56) References Cited

U.S. PATENT DOCUMENTS

| | | |
|---|---|---|
| 4,156,296 A | 5/1979 | Johnson et al. |
| 4,213,208 A | 7/1980 | Marne |
| 4,367,562 A | 1/1983 | Gauthier |

(Continued)

FOREIGN PATENT DOCUMENTS

| | | |
|---|---|---|
| FR | 2801189 A1 | 5/2001 |
| FR | 2935601 A1 | 3/2010 |

*Primary Examiner* — Larry E Waggle, Jr.
(74) *Attorney, Agent, or Firm* — Duane Morris LLP

(57) ABSTRACT

An implant for fusing adjacent bones is disclosed. The implant includes an elongate threaded member and a flexible portion extending from the elongate threaded member. The flexible portion includes a plurality of prongs configured to be reversibly compressed toward an axis defined by the elongate threaded member.

9 Claims, 23 Drawing Sheets

(51) Int. Cl.
*A61B 17/02* (2006.01)
*A61F 2/42* (2006.01)

(56) References Cited

U.S. PATENT DOCUMENTS

| | | | |
|---|---|---|---|
| 4,642,122 | A | 2/1987 | Steffee |
| 4,731,087 | A | 3/1988 | Sculco et al. |
| 4,908,031 | A | 3/1990 | Frisch |
| 4,932,974 | A | 6/1990 | Pappas et al. |
| 5,037,440 | A | 8/1991 | Koenig |
| 5,207,712 | A | 5/1993 | Cohen |
| 5,326,366 | A | 7/1994 | Pascarella et al. |
| 5,330,476 | A | 7/1994 | Hiot et al. |
| 5,354,301 | A | 10/1994 | Castellano |
| 5,425,776 | A | 6/1995 | Cohen |
| 5,458,648 | A | 10/1995 | Berman et al. |
| 5,480,447 | A | 1/1996 | Skiba |
| 5,484,443 | A | 1/1996 | Pascarella et al. |
| 5,529,075 | A | 6/1996 | Clark |
| 5,595,563 | A | 1/1997 | Moisdon |
| 5,669,913 | A | 9/1997 | Zobel |
| 5,683,466 | A | 11/1997 | Vitale |
| 5,725,585 | A | 3/1998 | Zobel |
| 5,776,202 | A | 7/1998 | Copf et al. |
| 5,919,139 | A | 7/1999 | Slavitt |
| 5,919,193 | A * | 7/1999 | Slavitt .............. 606/65 |
| 5,984,971 | A | 11/1999 | Faccioli et al. |
| 6,099,571 | A | 8/2000 | Knapp |
| 6,200,345 | B1 | 3/2001 | Morgan |
| 6,319,284 | B1 | 11/2001 | Rushdy et al. |
| 6,383,223 | B1 | 5/2002 | Baehler et al. |
| 7,041,106 | B1 | 5/2006 | Carver et al. |
| 7,044,953 | B2 * | 5/2006 | Capanni .............. 606/309 |
| 7,192,445 | B2 | 3/2007 | Ellingsen et al. |
| 7,291,175 | B1 | 11/2007 | Gordon |
| 7,909,880 | B1 | 3/2011 | Grant |
| 8,608,785 | B2 * | 12/2013 | Reed et al. .............. 606/305 |
| 2002/0072803 | A1 | 6/2002 | Saunders et al. |
| 2002/0111690 | A1 | 8/2002 | Hyde |
| 2003/0191422 | A1 | 10/2003 | Sossong |
| 2004/0097941 | A1 | 5/2004 | Weiner et al. |
| 2004/0230313 | A1 | 11/2004 | Saunders |
| 2005/0123672 | A1 | 6/2005 | Justin et al. |
| 2005/0187636 | A1 | 8/2005 | Graham |
| 2005/0283159 | A1 | 12/2005 | Amara |
| 2006/0074492 | A1 | 4/2006 | Frey |
| 2006/0100715 | A1 | 5/2006 | De Villiers |
| 2006/0129153 | A1 | 6/2006 | Klaue et al. |
| 2007/0078518 | A1 | 4/2007 | Lavi |
| 2007/0142920 | A1 | 6/2007 | Niemi |
| 2007/0213831 | A1 | 9/2007 | de Cubber |
| 2008/0051912 | A1 | 2/2008 | Hollawell |
| 2008/0086139 | A1 | 4/2008 | Bourke et al. |
| 2008/0177291 | A1 | 7/2008 | Jensen et al. |
| 2008/0177334 | A1 | 7/2008 | Stinnette |
| 2008/0195215 | A1 | 8/2008 | Morton |
| 2008/0221697 | A1 | 9/2008 | Graser |
| 2010/0131072 | A1 | 5/2010 | Schulte |
| 2010/0185295 | A1 | 7/2010 | Emmanuel |
| 2010/0249942 | A1 | 9/2010 | Goswami et al. |
| 2010/0262254 | A1 | 10/2010 | Lawrence et al. |
| 2011/0004255 | A1 | 1/2011 | Weiner et al. |
| 2011/0082507 | A1 | 4/2011 | Slaue |
| 2011/0082508 | A1 | 4/2011 | Reed |
| 2011/0093085 | A1 | 4/2011 | Morton |
| 2011/0144644 | A1 | 6/2011 | Prandi et al. |
| 2011/0257652 | A1 | 10/2011 | Roman |
| 2011/0301652 | A1 | 12/2011 | Reed et al. |
| 2011/0301653 | A1 | 12/2011 | Reed et al. |
| 2012/0065692 | A1 | 3/2012 | Champagne et al. |

* cited by examiner

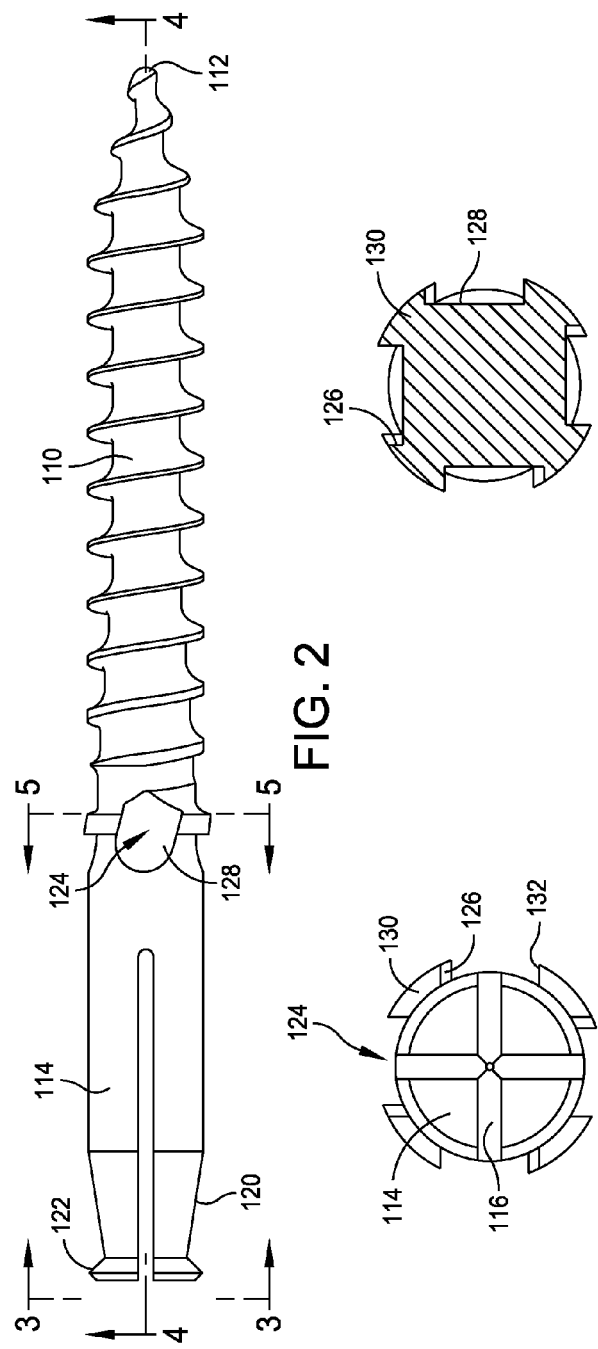
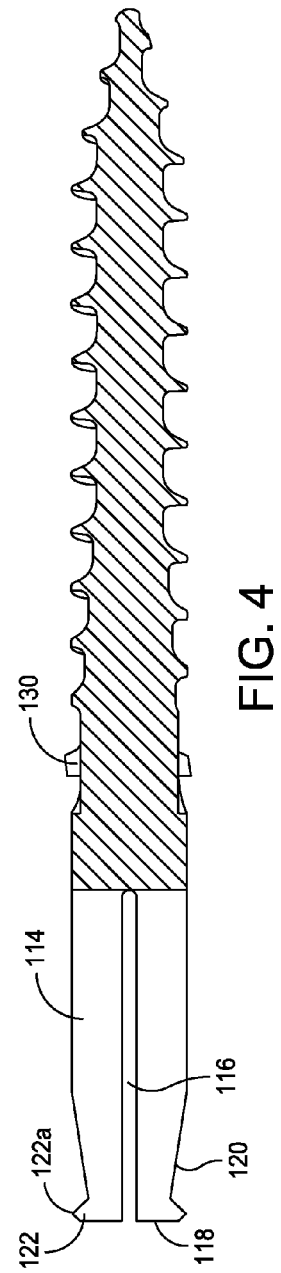

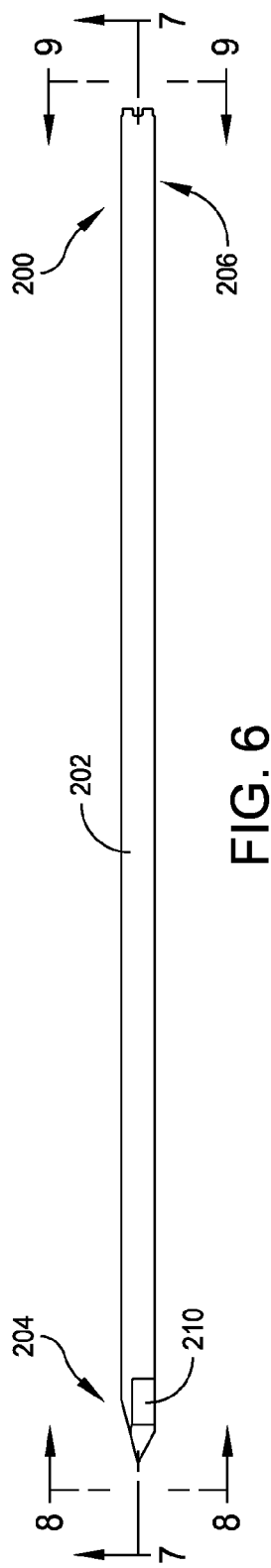
FIG. 6
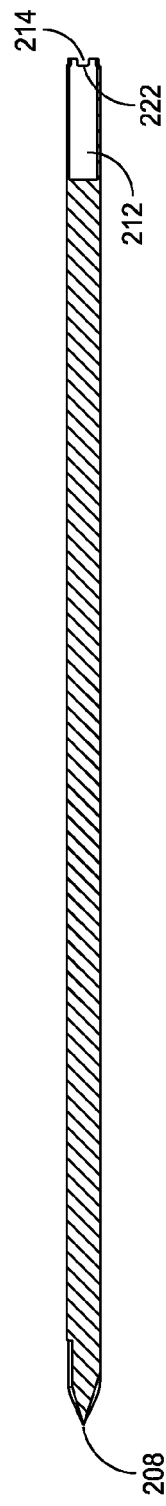
FIG. 7
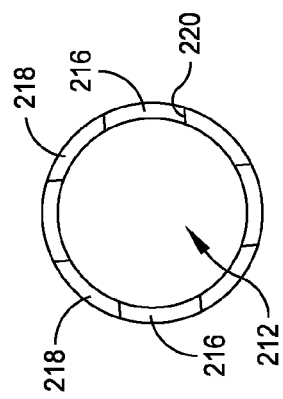
FIG. 9
FIG. 8

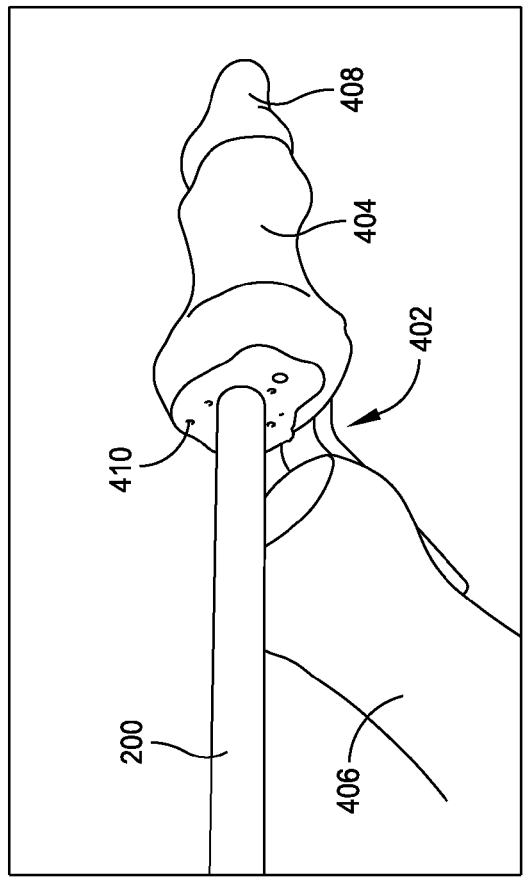
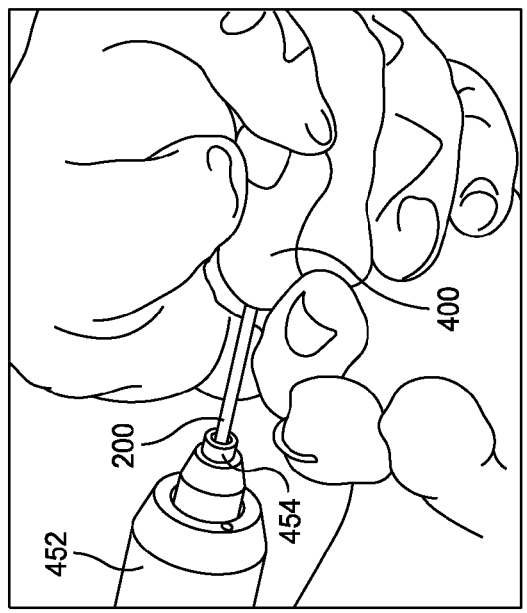
FIG. 15B
FIG. 15A

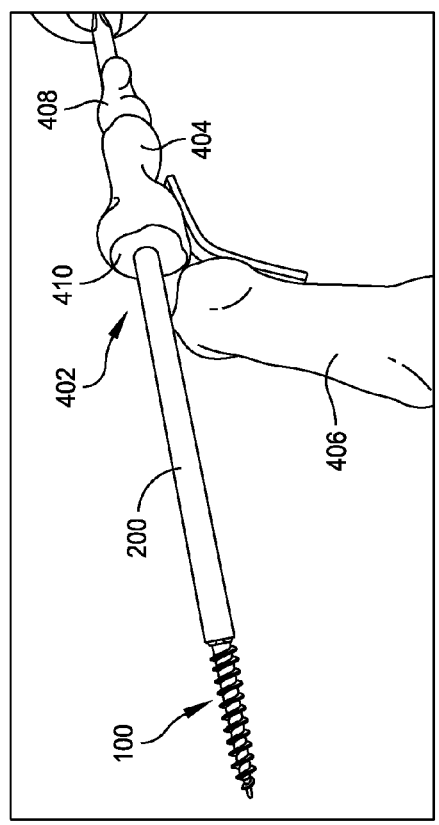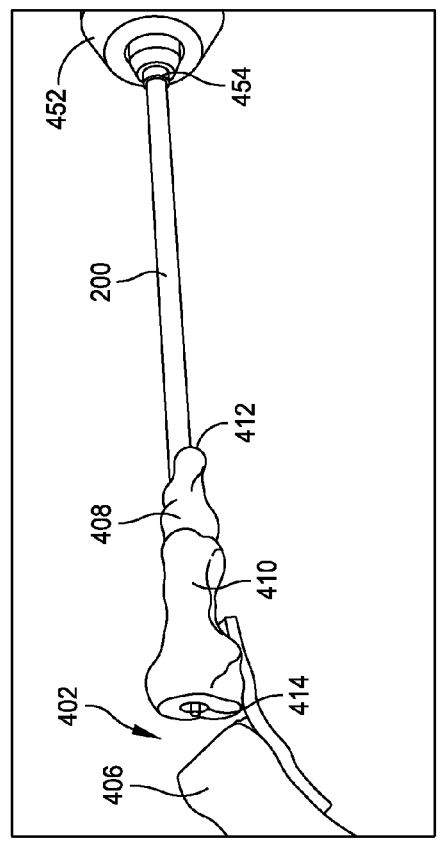
FIG. 17
FIG. 18

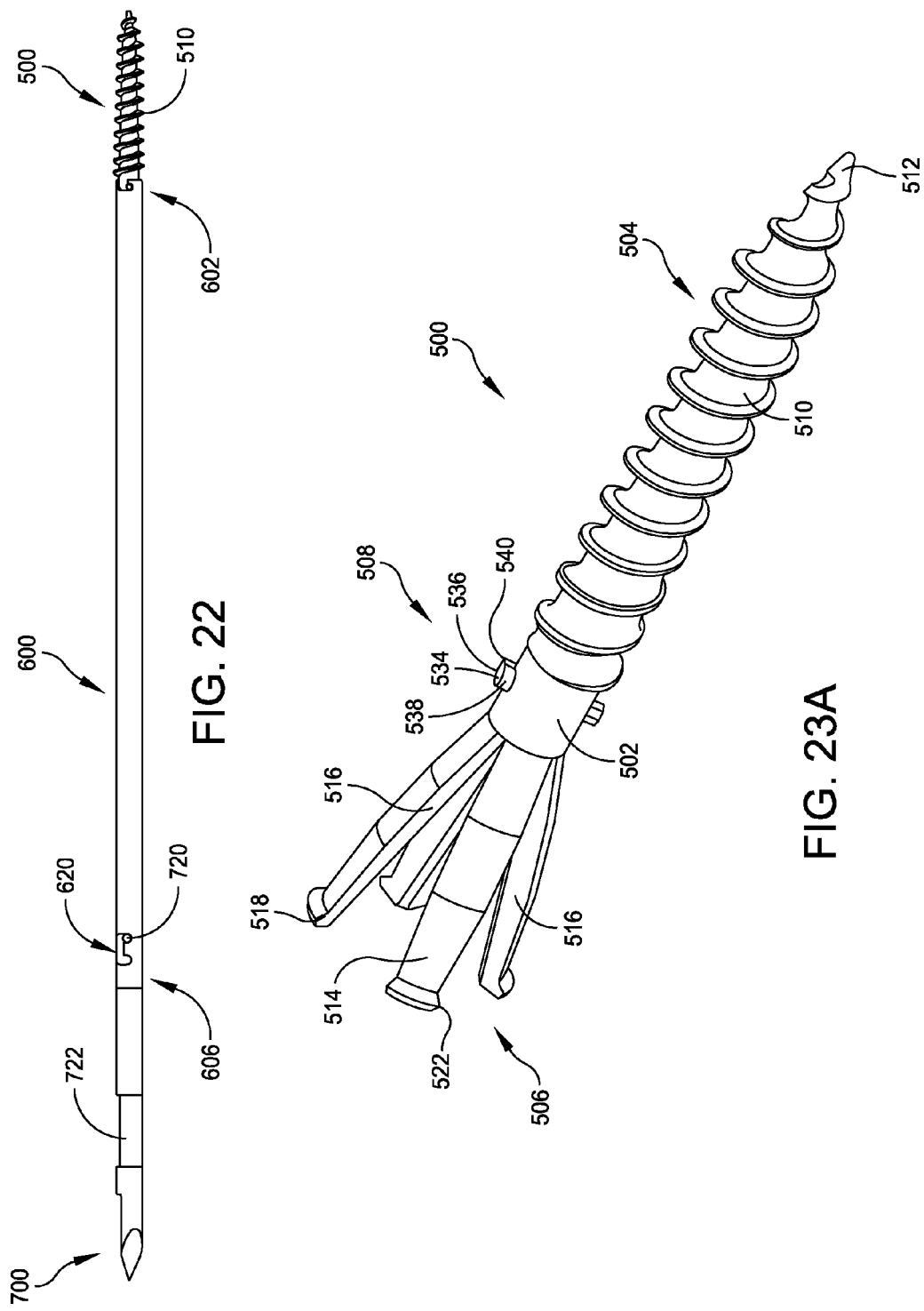

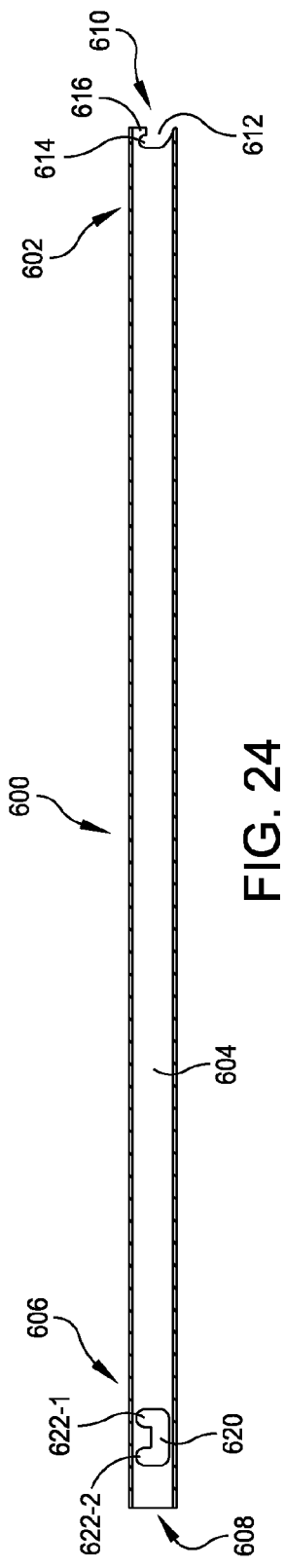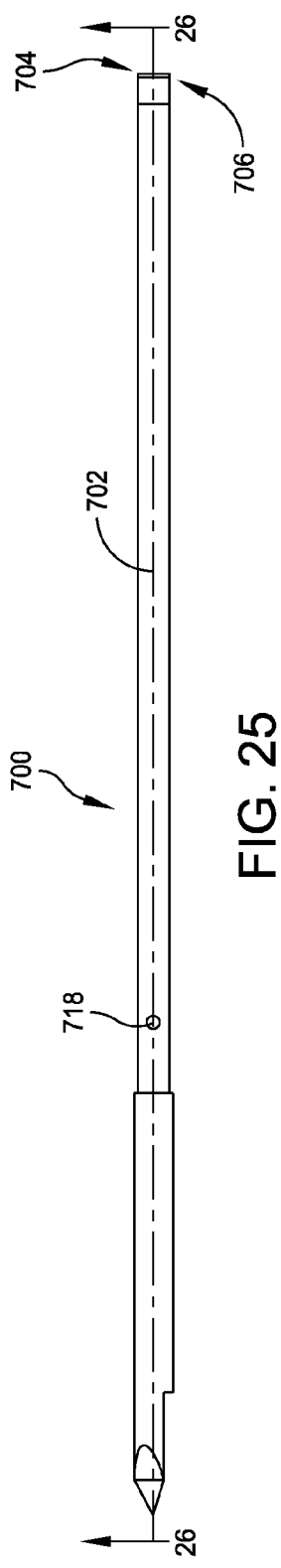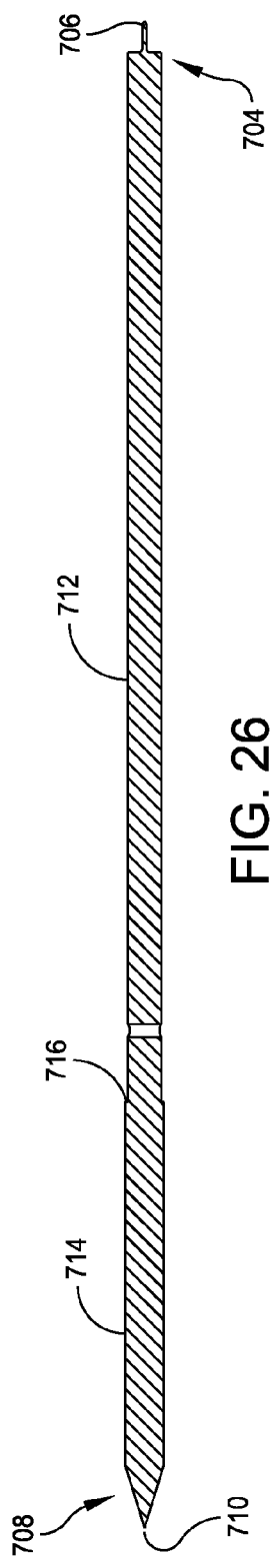

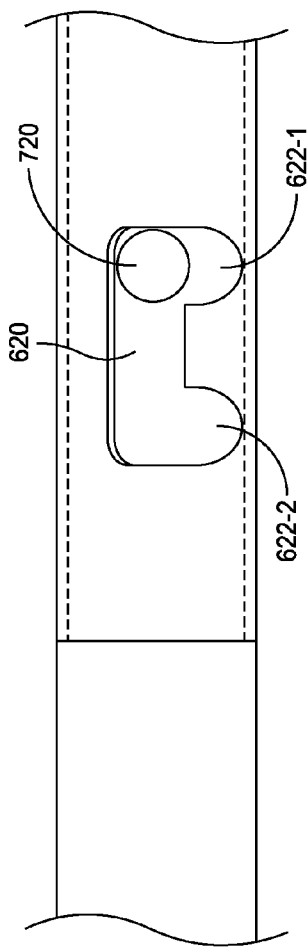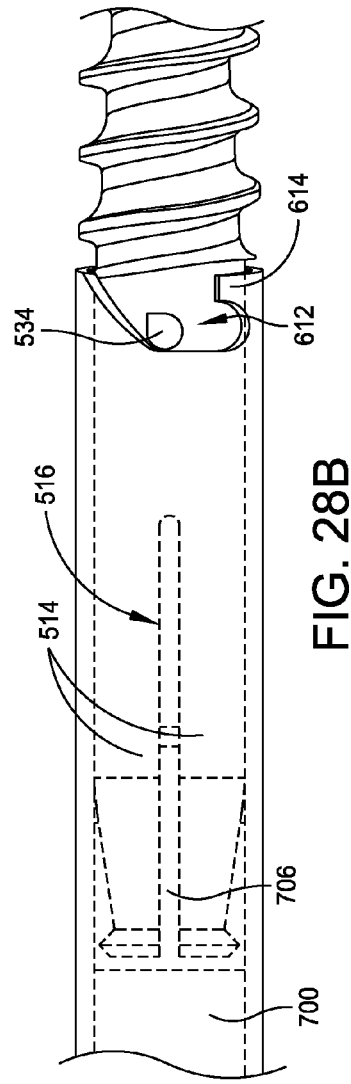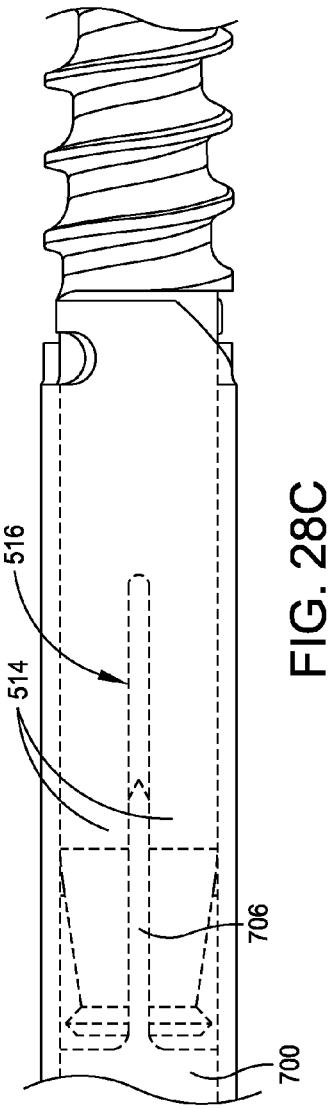

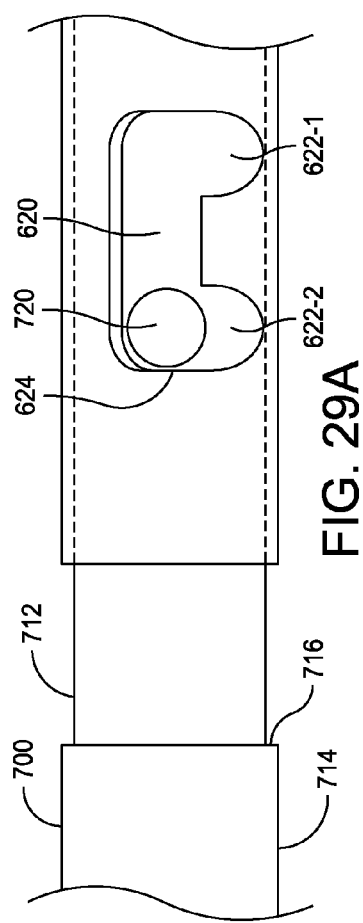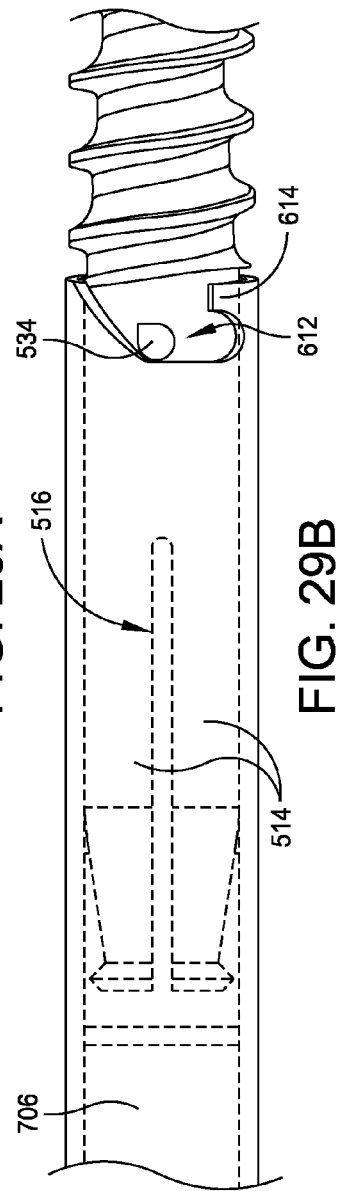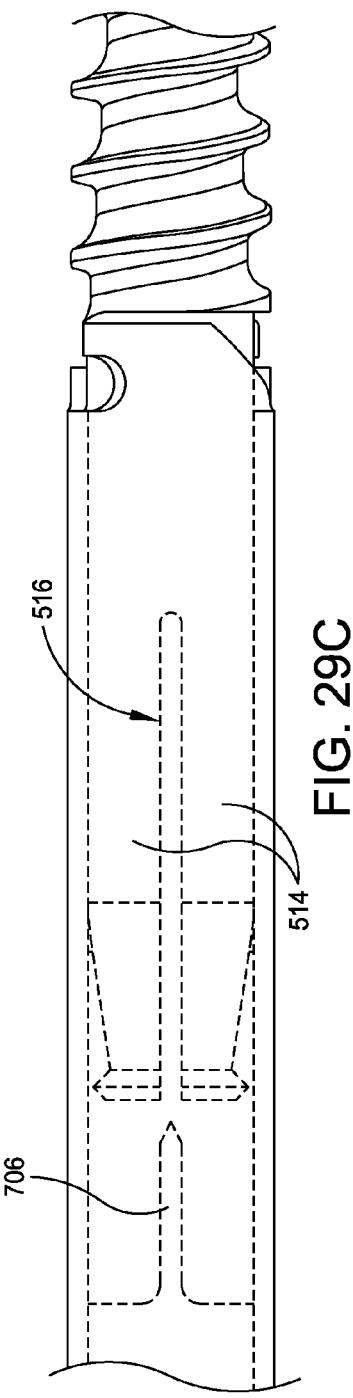

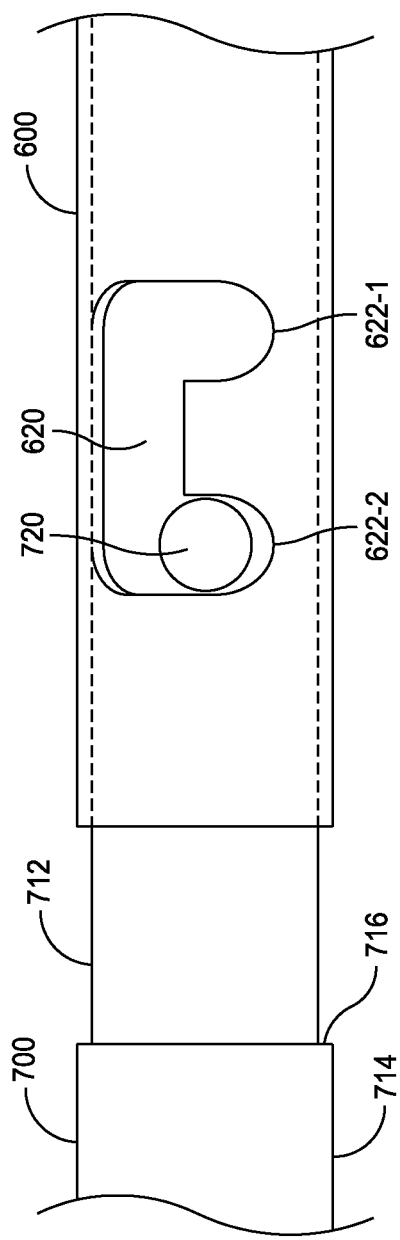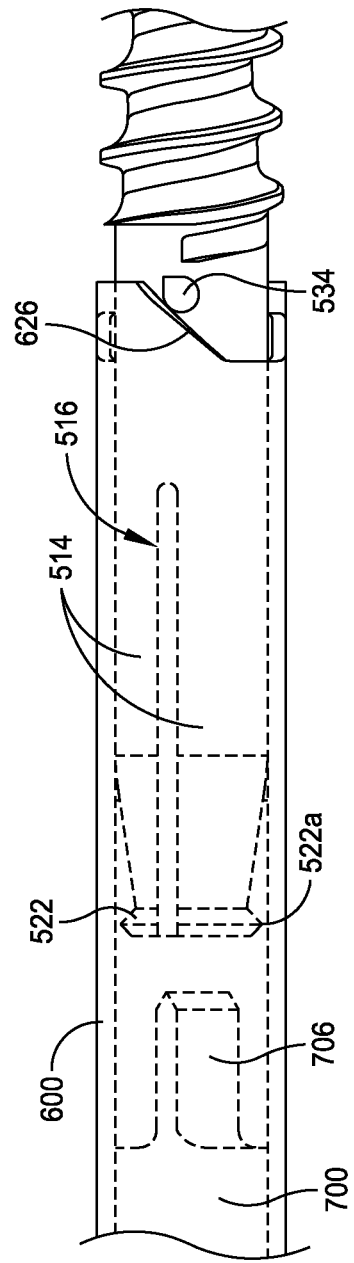
FIG. 30A
FIG. 30B

HAMMER TOE IMPLANT WITH EXPANSION PORTION FOR RETROGRADE APPROACH

CROSS-REFERENCE TO RELATED APPLICATIONS

This application is a Continuation of U.S. patent application No. 13/099,691, now U.S. Pat. No. 8,608,785, filed May 3, 2011, which claims priority to U.S. Provisional Patent Application No. 61/350,663, which was filed on Jun. 2, 2010, and to U.S. Provisional Patent Application No. 61/434,491, which was filed on Jan. 20, 2011, the entireties of which are herein incorporated by reference.

FIELD OF DISCLOSURE

The disclosed system and method relate implants. More specifically, the disclosed system and method relate to installing an implant for treating hammer toe.

BACKGROUND

Hammer toe is a deformity of the toe that affects the alignment of the bones adjacent to the proximal interphalangeal (PIP) joint. Hammer toe can cause pain and lead to difficulty in walking or wearing shoes. A hammer toe can often result in an open sore or wound on the foot. In some instances, surgery may be required to correct the deformity by fusing one or both of the PIP and distal interphalangeal (DIP) joints.

The most common corrective surgery includes the placement of a pin or rod in the distal, middle, and proximal phalanxes of the foot to fuse the PIP and DIP joints. The pin or rod is cut at the tip of the toe, externally of the body. A plastic or polymeric ball is placed over the exposed end of the rod, which remains in the foot of the patient until the PIP and/or DIP joints are fused in approximately 6 to 12 weeks. This conventional treatment has several drawbacks such as preventing the patient from wearing closed toe shoes while the rod or pin is in place, and the plastic or polymeric ball may snag a bed sheet or other object due to it extending from the tip of the toe resulting in substantial pain for the patient.

Another conventional implant includes a pair of threaded members that are disposed within adjacent bones of a patient's foot. The implants are then coupled to one another through male-female connection mechanism, which is difficult to install in situ and has a tendency to separate.

Yet another conventional implant has body including an oval head and a pair of feet, which are initially compressed. The implant is formed from nitinol and is refrigerated until it is ready to be installed. The head and feet of the implant expand due to the rising temperature of the implant to provide an outward force on the surrounding bone when installed. However, the temperature sensitive material may result in the implant deploying or expanding prior to being installed, which requires a new implant to be used.

Accordingly, an improved implant for treating hammer toe is desirable.

SUMMARY

An implant for fusing adjacent bones is disclosed. The implant includes an elongate threaded member and a flexible portion extending from the elongate threaded member. The flexible portion includes a plurality of prongs configured to be reversibly compressed toward an axis defined by the elongate threaded member.

An implant system is also disclosed. The implant system includes an implant comprising an elongate threaded member and a flexible portion extending from the elongate threaded member. The flexible portion includes a plurality of prongs configured to be reversibly compressed toward an axis defined by the elongate threaded member. A core pin for driving the implant into bone includes an elongate body having a pointed tip at one end and a fin disposed at an opposite end. The fin is sized and configured to be received within a slot defined by the prongs of the implant. A tube defines a passageway extending from an implant engaging end to a core pin engaging end and being sized and configured to receive the prongs of the implant and a first portion of the core pin therein.

Also disclosed is a method of connecting adjacent bones. The method includes forming an incision to gain access to a joint between first and second bones, flexing the first and second bones such that the bones are disposed at an angle from one another, and inserting a pointed tip of a core pin extending from a first end of a tube into a first end of a first bone until a tip of an elongate threaded member of an implant extending from and at least partially disposed within a second end of the tube is received within an intramedullary channel formed by the core pin and tube. The first end of the first bone is closer to the second bone compared to a second end of the first bone. The first and second bones are repositioned such that they are approximately linearly aligned with each other. The core pin is rotated in a first direction to drive the elongate threaded member into the second bone. The core pin is decoupled from its engagement with the implant, and the core pin and tube are withdrawn from the first bone to disengage the second end of the tube from a flexible portion of the implant including a plurality of prongs. The plurality of prongs outwardly flex to contact the first bone when disengaged from the second end of the tube.

BRIEF DESCRIPTION OF THE DRAWINGS

These and other features and advantages of the present invention will be more fully disclosed in, or rendered obvious by the following detailed description of the preferred embodiments of the invention, which are to be considered together with the accompanying drawings wherein like numbers refer to like parts and further wherein:

FIG. 2 is a plan view of the improved implant for treating hammer toe illustrated in FIG. 1B;

FIG. 3 is an end view of the flexible portion of the implant taken along line 3-3 in FIG. 2;

FIG. 4 is a sectional view of the implant taken along line 4-4 in FIG. 2;

FIG. 5 is a cross-sectional view of the implant taken along line 5-5 in FIG. 2;

FIG. 6 is a side plan view of one example of driving wire for driving the implant illustrated in FIGS. 1A-5 into bone;

FIG. 7 is a sectional view of the driving wire taken along line 7-7 in FIG. 6;

FIG. 8 is an end view of the driving wire taken along line 8-8 in FIG. 6;

FIG. 9 is an end view of the driving wire taken along line 9-9 in FIG. 6;

FIGS. 15A-15B illustrate the drilling through the middle and distal phalanxes of a foot;

FIG. 17 illustrates a driving tool being disengaged from an end of the driving wire coupled to an implant and being attached to an end of the driving wire including a trocar tip;

FIG. 18 illustrates the implant coupled to an end of the driving wire being received within the intramedullary channel formed in the middle phalanx;

FIG. 22 is a plan view of one example of an assemblage of an implant, a tube, and a driving core;

FIG. 23A is an isometric view of another example of a hammer toe implant in its natural or uncompressed state;

FIG. 24 is a cross-sectional view of the tube illustrated in FIG. 22 taken along the length of the tube;

FIG. 25 is a plan view of one example of a driving core in accordance with FIG. 22;

FIG. 26 is a cross-sectional view of the driving core taken along line 26-26 in FIG. 25;

FIG. 28A illustrates the interface between the driving core and the tube illustrated in FIG. 22 at a second stage of implanting the implant;

FIGS. 28B and 28C illustrate the interface between the blade of the driving core and the implant disposed within the tube at the second stage of implanting the implant;

FIG. 29A illustrates the interface between the driving core and the tube illustrated in FIG. 22 at a third stage of implanting the implant;

FIGS. 29B and 29C illustrate the interface between the blade of the driving core and the implant disposed within the tube at the third stage of implanting the implant;

FIG. 30A illustrates the interface between the driving core and the tube illustrated in FIG. 22 at a fourth stage of implanting the implant;

FIG. 30B illustrates the interface between the blade of the driving core and the implant disposed within the tube at the fourth stage of implanting the implant;

DETAILED DESCRIPTION

Figure 1A:
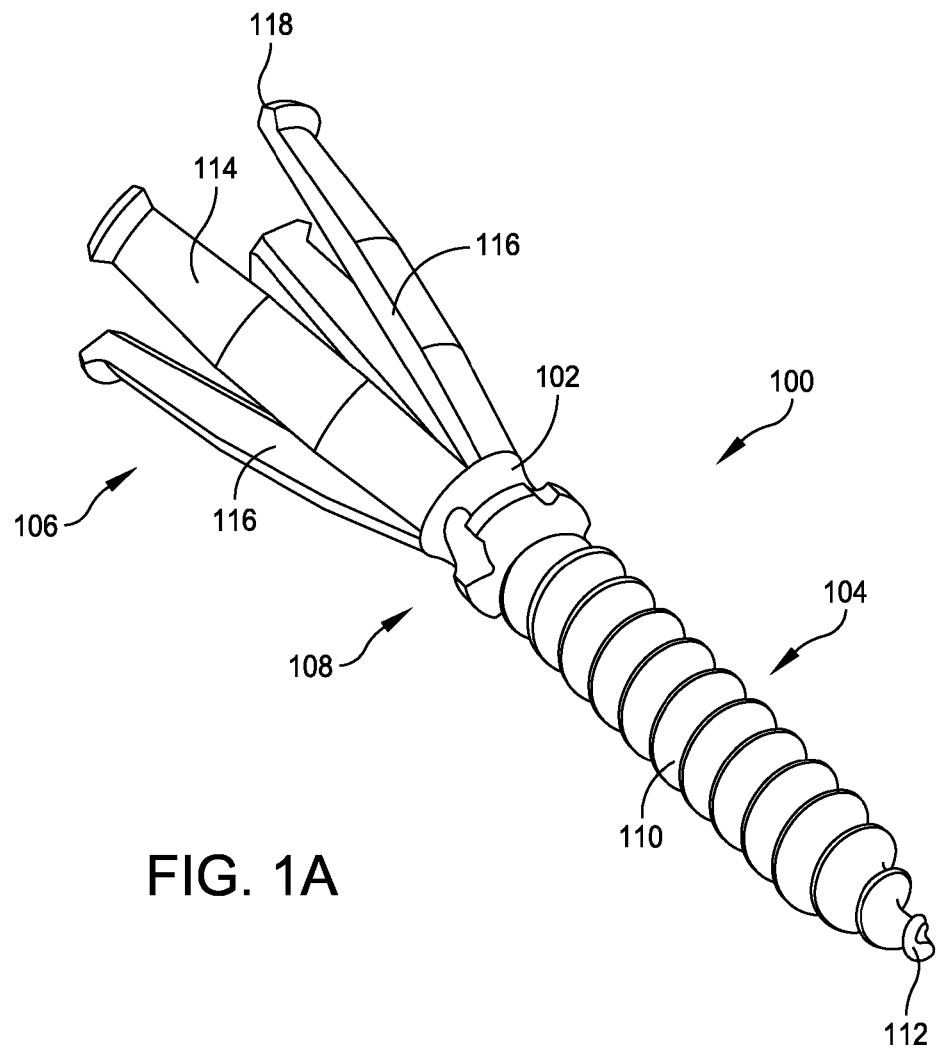
FIG. 1A is an isometric view of an improved implant for treating hammer toe in an uncompressed or natural state.

This description of preferred embodiments is intended to be read in connection with the accompanying drawings, which are to be considered part of the entire written description. The drawing figures are not necessarily to scale and certain features of the invention may be shown exaggerated in scale or in somewhat schematic form in the interest of clarity and conciseness. In the description, relative terms such as "horizontal," "vertical," "up," "down," "top," and "bottom" as well as derivatives thereof (e.g., "horizontally," "downwardly," "upwardly," etc.) should be construed to refer to the orientation as then described or as shown in the drawing figure under discussion. These relative terms are for convenience of description and normally are not intended to require a particular orientation. Terms including "inwardly" versus "outwardly," "longitudinal" versus "lateral," and the like are to be interpreted relative to one another or relative to an axis of elongation, or an axis or center of rotation, as appropriate. Terms concerning attachments, coupling, and the like, such as "connected" and "interconnected," refer to a relationship wherein structures are secured or attached to one another either directly or indirectly through intervening structures, as well as both movable or rigid attachments or relationships, unless expressly described otherwise. The term "operatively connected" is such an attachment, coupling or connection that allows the pertinent structures to operate as intended by virtue of that relationship.

Unless otherwise stated, all percentages, parts, ratios, or the like are by weight. When an amount, concentration, or other value or parameter is given as either a range, preferred range, or a list of upper preferable values and lower preferable values, this is understood as specifically disclosing all ranges formed from any pair of any upper range limit or preferred value and any lower range limit or preferred value regardless of whether those ranges are explicitly disclosed.

Figure 1B:
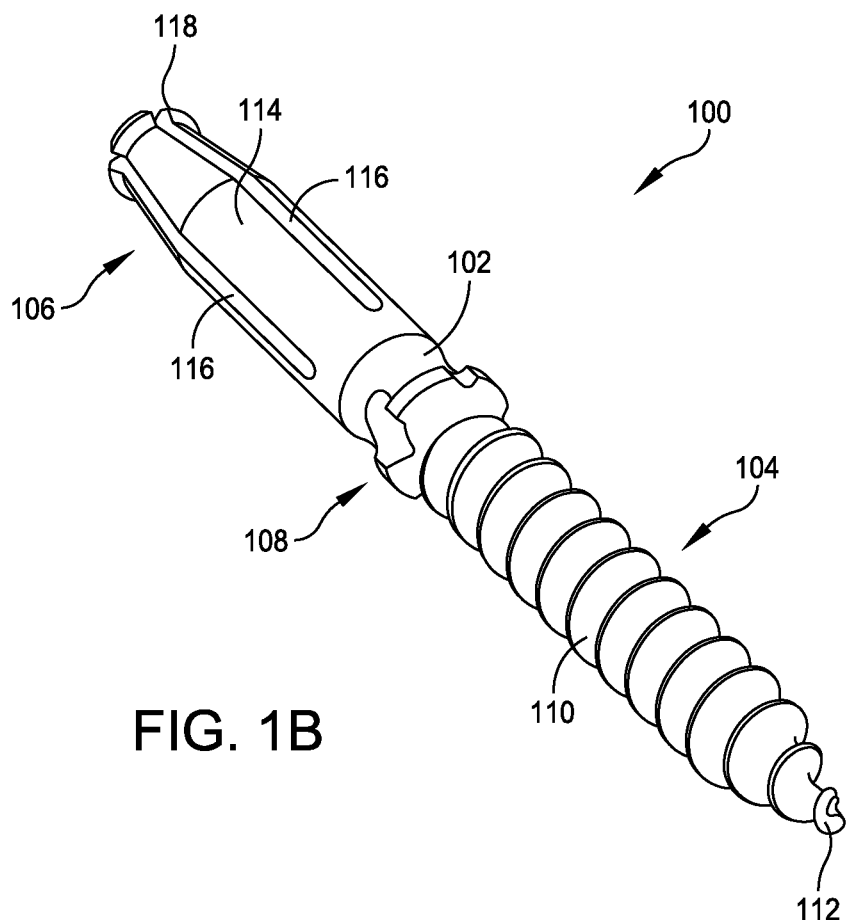
FIG. 1B is an isometric view of the improved implant illustrated in FIG. 1A in which the implant is in a compressed state.

Referring to FIGS. 1A and 1B, an implant 100 formed in accordance with one embodiment of the invention includes an elongate body 102 having a threaded portion 104 and a flexible portion 106, which are joined together at an engagement portion 108. Implant 100 may be provided in a variety of lengths and widths for implantation in the distal and middle phalanxes of a foot. In one example, implant 100 has a length of approximately 2.1 centimeters (approximately 0.825 inches) and a maximum outer diameter of approximately 0.24 centimeters (approximately 0.094 inches). Implant 100 may be formed from any material suitable for implanting into living tissue including, but not limited to, stainless steel, nitinol, aluminum, polymer, or the like. Fabricating implant 100 from nitinol, or another shape memory or super elastic alloy, may advantageously enhance resistance to movement of the implant when positioned in a foot, as described below.

Threaded portion 104 includes a plurality of threads 110 that taper to a tip 112 for cutting into bone. In some embodiments, threaded portion 104 has a length of approximately 1.3 centimeters (approximately 0.51 inches) and a diameter of approximately 0.2 centimeters (approximately 0.079 inches), although one skilled in the art will understand that threaded portion 104 may have other dimensions. For example, threaded portion 104 may have lengths of approximately 1 centimeter or 1.6 centimeter, to list a couple of alternative lengths.

Flexible portion 106 includes a plurality of prongs 114 formed by lengthwise slots 116 defined in body 102. For example, flexible portion 106 may include two, three, four or more prongs 114 formed by two slots 116 orthogonally disposed from one another. One skilled in the art will understand that slots 116 may be disposed at other angles with respect to each other. In some embodiments, slots 116 extend approximately 0.57 centimeters (approximately 0.224 inches) from end 118 of flexible portion 106. One skilled in the art will understand that slots 116 may have a length that is less than half a length of flexible portion 106 or approximately equal to the length of flexible portion 106. Each of prongs 114 may include a taper section 120 that tapers from a first diameter, which may be 0.2 centimeters (approximately 0.079 inches) to a second diameter of approximately 0.14 centimeters (approximately 0.055 inches) over a length of approximately 0.18 centimeters (0.071 inches). Each taper 120 may terminate at an outwardly projecting anti-rotational feature 122, which may have a triangular cross-section geometry as best seen in FIGS. 2 and 4.

Engagement portion 108 may have a circular cross-sectional area having a plurality of notches 124 as best seen in FIGS. 1 and 3. Each notch 124 may include a pair of opposed side walls 126 separated by a bottom wall 128. In some embodiments, notches 124 have a depth of approximately 0.03 centimeters (approximately 0.012 inches) and a width of approximately 0.1 centimeters (approximately 0.04 inches), although one skilled in the art will understand that number of notches 124 and their respective dimensions may be varied. As best seen in FIGS. 2 and 3, notches 124 may be formed at an angle with respect to the longitudinal axis defined by implant 100 to create projections 130 having pointed edges 132 to enhance engagement with driving wire 200. In some embodiments, the angle may be between 0 and 45 degrees with respect to the longitudinal axis of the implant 100, and particularly between 10 and 20 degrees with respect to the longitudinal axis defined by the implant 100, and even more particularly approximately 15 degrees with respect to the longitudinal axis defined by the implant 100.

Implant 100 is configured to be installed using a driving wire 200 such as the one illustrated in FIGS. 5-8. As shown in FIG. 5, driving wire 200 has an elongate body 202 having a trocar end 204 and an engagement end 206. The driving wire 200 may have an overall length of approximately 10.16 centimeters (approximately 4 inches) and an outer diameter of approximately 0.25 centimeters (approximately 0.098 inches), although one skilled in the art will understand that the dimensions of the driving wire 200 may be varied. Trocar end 204 has a pointed trocar tip 208, which may include a small flat 210 that may extend approximate 0.63 centimeters (approximately 0.25 inches) from the trocar tip 208. Driving wire 200 may be fabricated from any medically compatible material suitably rigid for drilling through bone including, but not limited to, stainless steel, steel, and aluminum to name a few.

Engagement end 206 defines a blind hole 212 having an internal diameter sized and configured to receive the flexible portion of implant 100. In some embodiments, the internal diameter of blind hole 212 is approximately 0.21 centimeters (approximately 0.08 inches) and extends approximately 0.89 centimeters (approximately 0.35 inches) from tip 214 of engagement end 206. As best seen in FIGS. 6 and 8, engagement end 206 includes a plurality of tabs 216 separated by notches 218. Tabs 216 are sized and arranged to be received in notches 124 of implant 100, and notches 218 are sized and arranged to receive projections 130 of implant 100. For example, notches 218 may have a width of approximately 0.09 centimeters (approximately 0.035 inches) and extend to a depth of approximately 0.05 centimeters (approximately 0.02 inches) from the tip 214 of engagement end 206. Additionally, notches 218 may be formed such that sidewalls 220 are angled with respect to the longitudinal axis defined by the elongate body 202. For example, the angle may be between 0 and 45 degrees with respect to the axis, and more particularly between 10 and 20 degrees.

Figure 10:
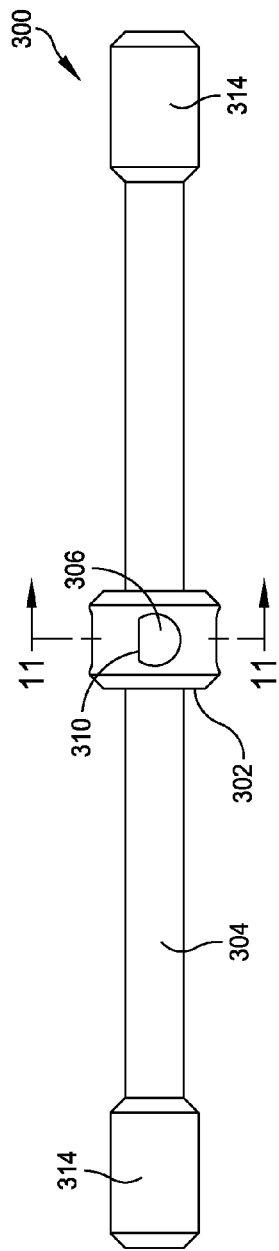
FIG. 10 is a top side view of a handle configured to engage the driving wire illustrated in FIG. 6.
Figure 11:
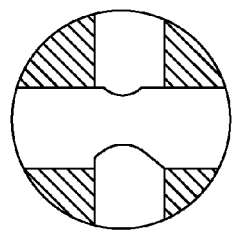
FIG. 11 is a cross-sectional view of the body of the handle taken along line 11-11 in FIG. 10.

One or more implants 100 of various sizes may be provided in a kit along with one or more driving wires 200 and a handle 300 such as the one illustrated in FIGS. 9-11. As best seen in FIG. 10, handle 300 includes a circular body 302 that slidingly receives an elongate member 304 having a pair of oppositely spaced retaining elements 314 disposed at either end to maintain engagement between body 302 and elongate member 304. Handle 300 may be formed from any material suitably rigid for driving wire 200 and implant 100 into bone including, but not limited to stainless steel, steel, aluminum, polymer, or plastic to name a few.

Body 302 defines first and second apertures 306, 308, which extend through body 302 and intersect with one another. In some embodiments, apertures 306 and 308 may have different dimensions for engaging differently sized driving wires 200. For example, aperture 306 may have a radius of approximately 0.13 centimeters (0.05 inches) with the flat 310 having a distance of approximately 0.21 centimeters (approximately 0.08 inches) from the apex of the aperture 306 opposite flat 310, and aperture 308 may have a radius of approximately 0.16 centimeters (approximately 0.06 inches) with flat 312 having a distance of approximately 0.25 centimeters (approximately 0.1 inches) from the apex of aperture 308 opposite flat 312.

Figure 13:
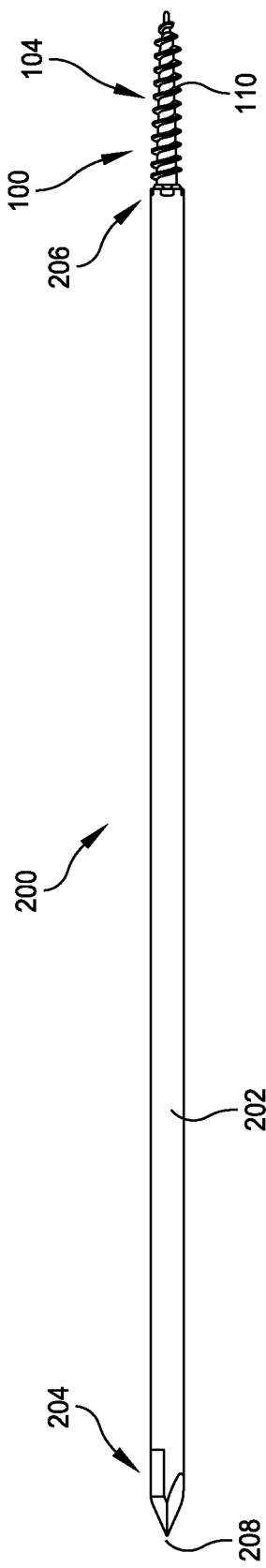
FIG. 13 illustrates the flexible portion of the implant disposed within a blind hole defined by an engagement portion of the driving wire.

The method of installing an implant 100 via a retrograde approach between the proximal and middle phalanxes is now described with reference to FIGS. 13-20. One skilled in the art will understand that the method described herein may be applied to the middle and distal phalanxes or other adjacent bones. FIG. 13 illustrates the implant 100 having its flexible portion 106 received within the blind hole 212 defined by the engagement end 206 of the driving wire 200 as prongs 114 are compressed towards one another. In this configuration, projections 130 of engagement portion 108 of implant 100 are at least partially received within notches 218 of engagement end 206 of driving wire 200 and threaded portion 104 of implant 100 having threads 110 extends from the tip 214 of engagement end 206.

Figure 14B:
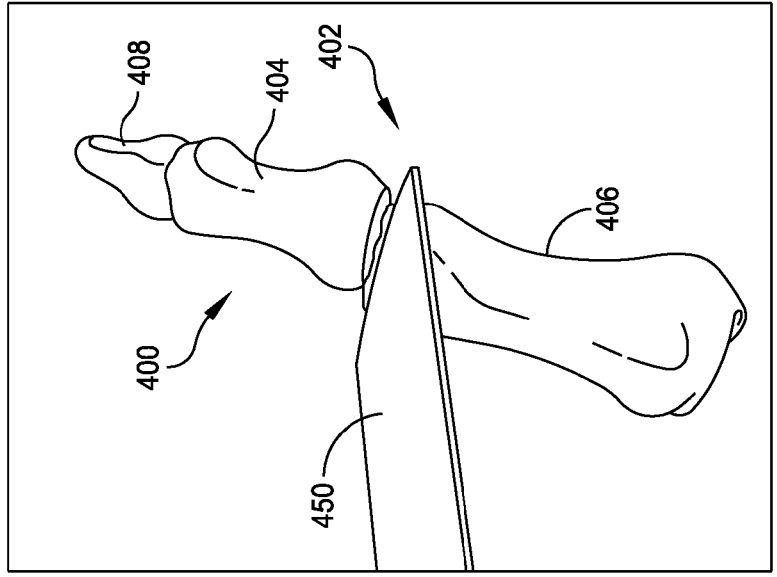
FIGS. 14A-B illustrate the middle and proximal phalanxes of a foot being resected.
Figure 14A:
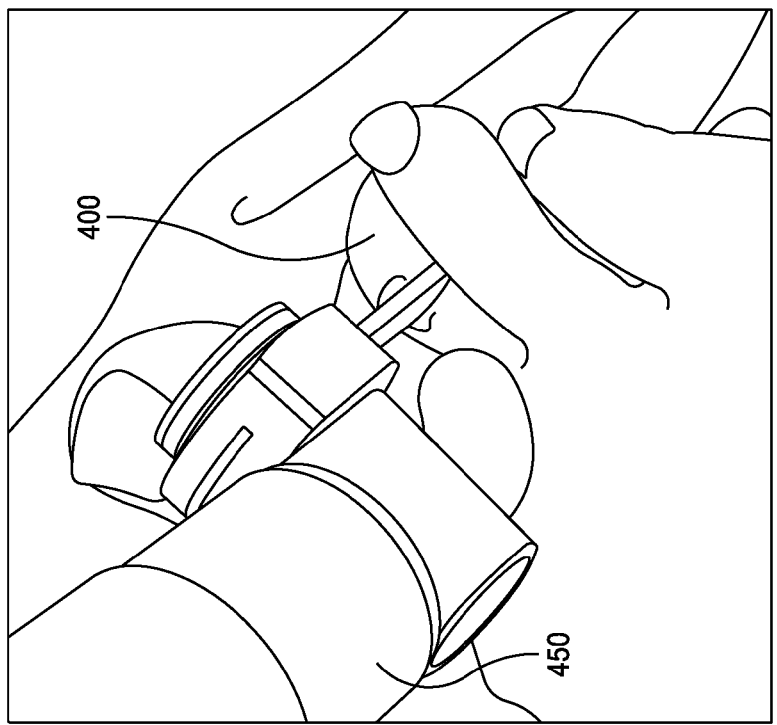

To install the implant, a toe 400 is opened to provide access to a joint 402 between a middle phalanx 404 and proximal phalanx 406, and middle and proximal phalanxes 404, 406 may be resected using a bone saw or other tool 450, as shown in FIGS. 14A and 14B. Engagement end 206 of driving wire 200, with implant 100 disposed within blind hole 212, may be received within chuck 454 of a drill 452, and trocar end 204 of driving wire 200 may be driven retrograde into the middle of proximal surface 410 of middle phalanx 404, as illustrated in FIGS. 15A and 15B.

Figure 16:
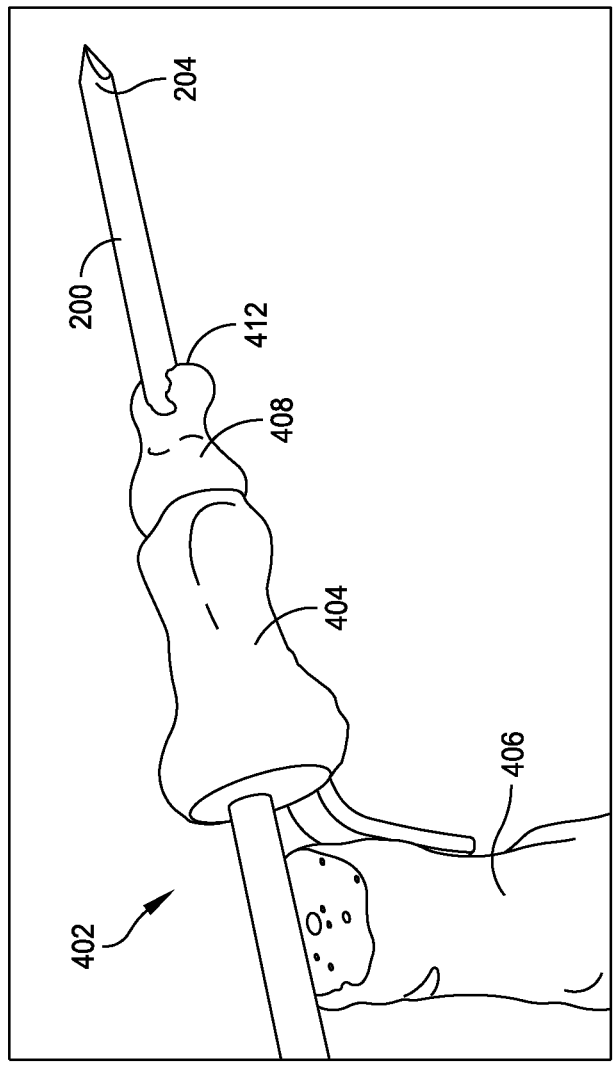
FIG. 16 illustrates passing the trocar through the middle and distal phalanxes of a foot.

Driving wire 200 is driven by drill 452 until trocar end 204 passes through middle phalanx 404 and distal phalanx 408 and out of distal tip 412 of distal phalanx 408, as shown in FIG. 16. With trocar end 204 extending from distal tip 412 of distal phalanx 408, chuck 454 of drill 452 may be loosened and removed from engaging implant 100 and engagement end 206 of driving wire 200. Drill 452 or handle 300 may then engage trocar end 204 of driving wire 200, as shown in FIG. 17.

Figure 19:
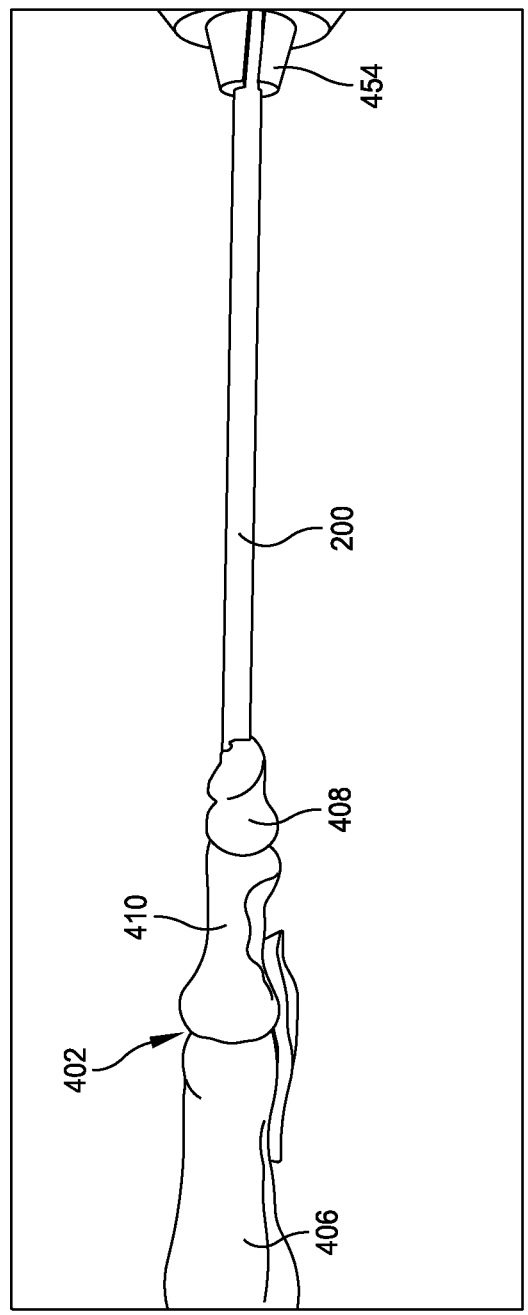
FIG. 19 illustrates the distal, middle, and proximal phalanxes being aligned.
Figure 20:
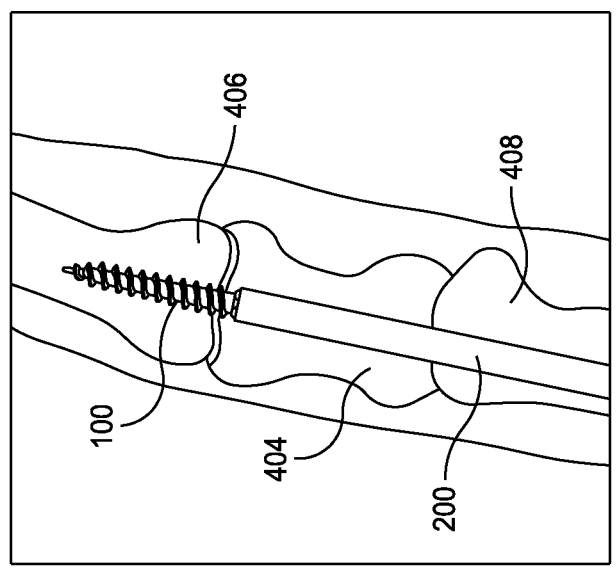
FIG. 20 illustrates the implant disposed within proximal phalanx.

Driving wire 200 is distally advanced until implant 100 is received within intramedullary channel 414 formed by driving wire 200, as shown in FIG. 18. With tip 112 of implant 100 received within intramedullary channel 414, middle phalanx 404 and proximal phalanx 406 are linearly aligned with each other, as shown in FIG. 19, and drill 452 or handle 300 is used to turn driving wire 200 in a clockwise direction to advance threads 110 of implant into proximal phalanx 406, as shown in FIG. 20. One skilled in the art will understand that threads 110 may also be left-handed threads such that turning driving wire 200 in a counterclockwise direction advances threads 110 into proximal phalanx 406.

With implant 100 secured across joint 402, driving wire 200 is retracted and turned in an opposite direction with respect to the direction in which it was turned to advance threads 110 into proximal phalanx 406 while retracting driving wire. Rotating driving wire 200 in an opposite direction while retracting it, e.g., distally advancing driving wire 200, causes a camming action between angled tabs 216 of driving wire 200 and the angle projections of implant 100 to assist in retracting driving 200 from intramedullary canal 414.

Figure 21:
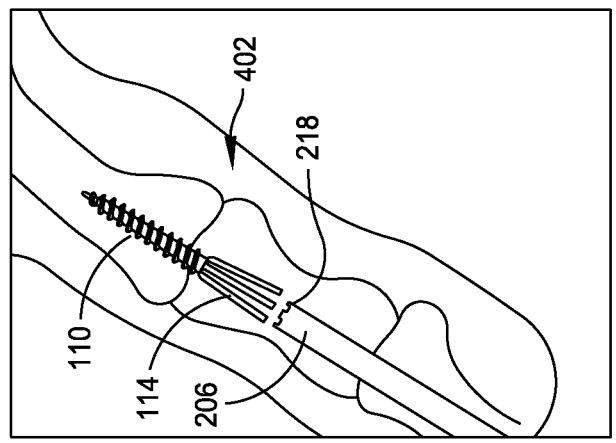
FIG. 21 illustrates the implant disposed across the proximal interphalangeal joint as the driving wire is withdrawn.

Driving wire 200 may be fully retracted from intramedullary canal 414. The removal of driving wire 200 from intramedullary canal 414 releases prongs 114 of implant 100, which were compressed within blind hole 212 of driving wire 200. If implant 100 is formed from a shape memory material such as, for example, nitinol, then prongs 114 may radially flex towards their natural or uncompressed state, as illustrated in FIG. 21, such that an edge 122a of anti-rotational feature 122 of prongs 114 engages the adjacent bone.

FIGS. 22-30B illustrate another embodiment of an implant 500 having a similar configuration to implant 100 in which like elements of implant 500 have the same reference numerals as the elements of implant 100 increased by 400. Engagement portion 508 has a circular cross-sectional geometry and includes one or more prominences 534 radially extending from body 502. As best seen in FIG. 27B, prominence or pin 534 is substantially cylindrical with first and second flats 536, 538 formed thereon. Flats 536, 538 extend away from each other in approximately normal directions from point 540.

Figure 31A:
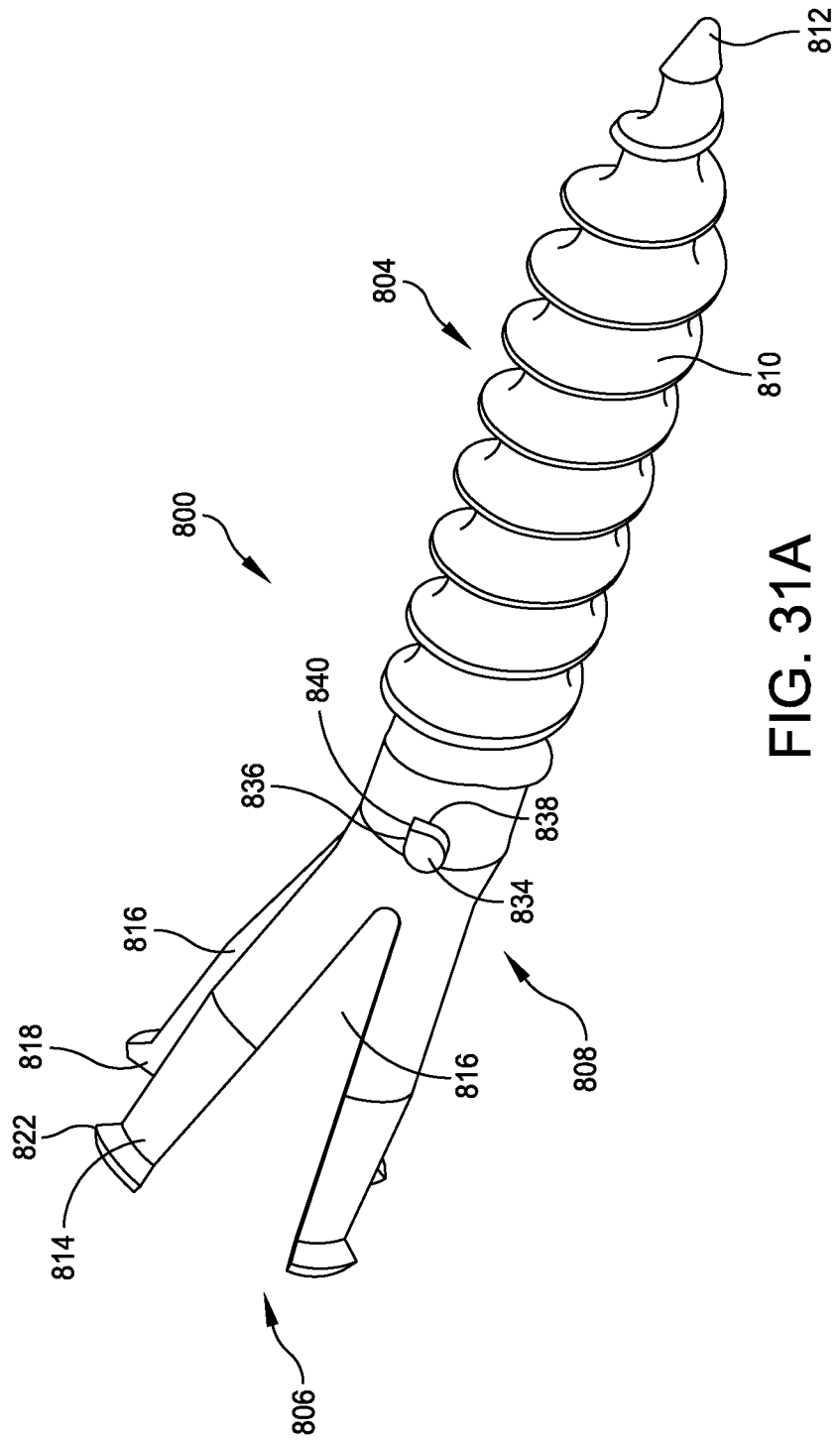
FIG. 31A is an isometric view of another example of a hammer toe implant in its natural or uncompressed state.
Figure 31B:
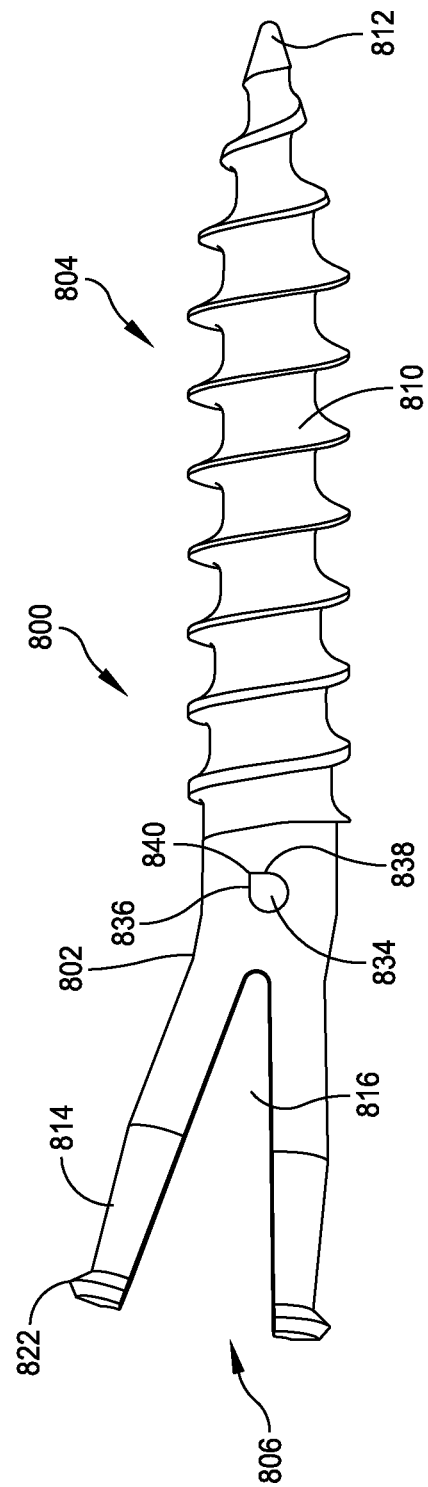
FIG. 31B is a side view of the hammer toe implant illustrated in FIG. 31A.
Figure 31C:
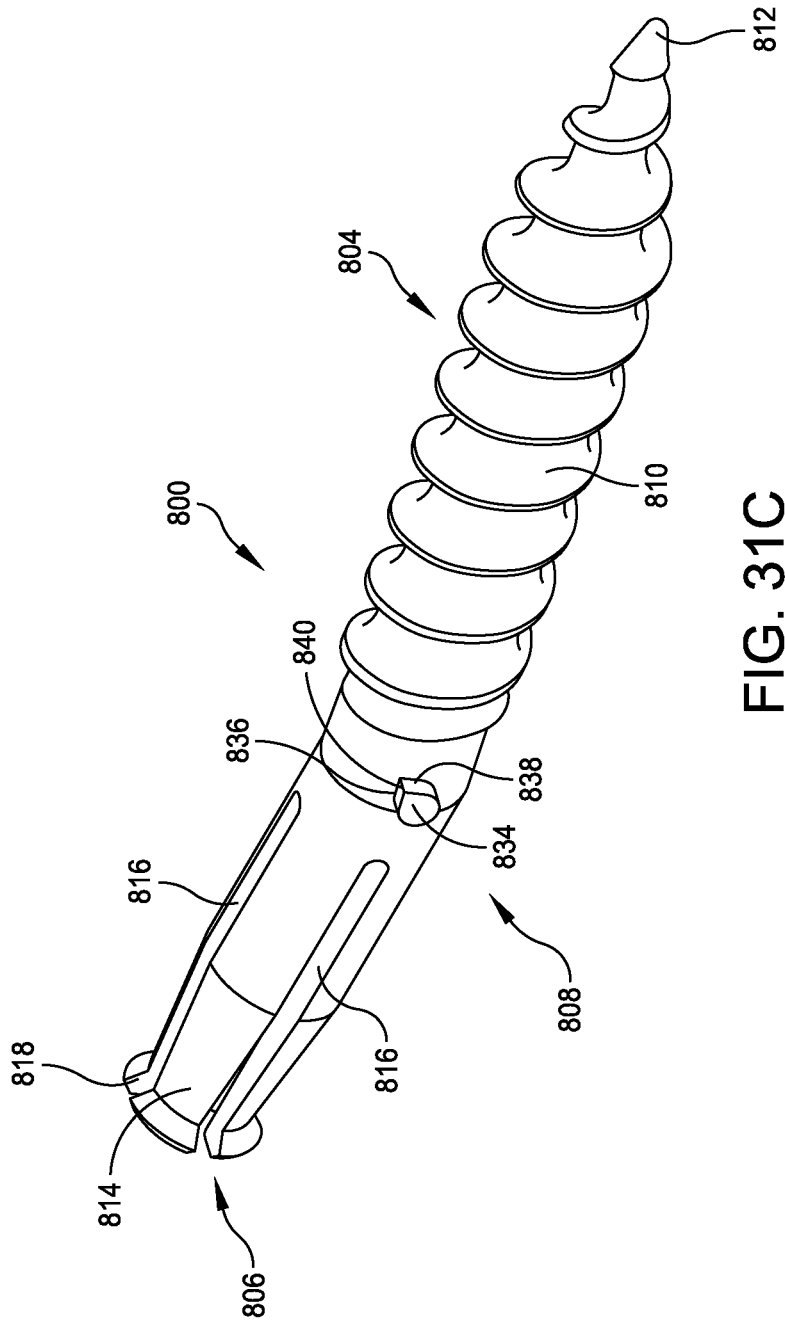
FIG. 31C is an isometric view of the hammer toe implant illustrated in FIG. 31A in its compressed state.
Figure 31D:
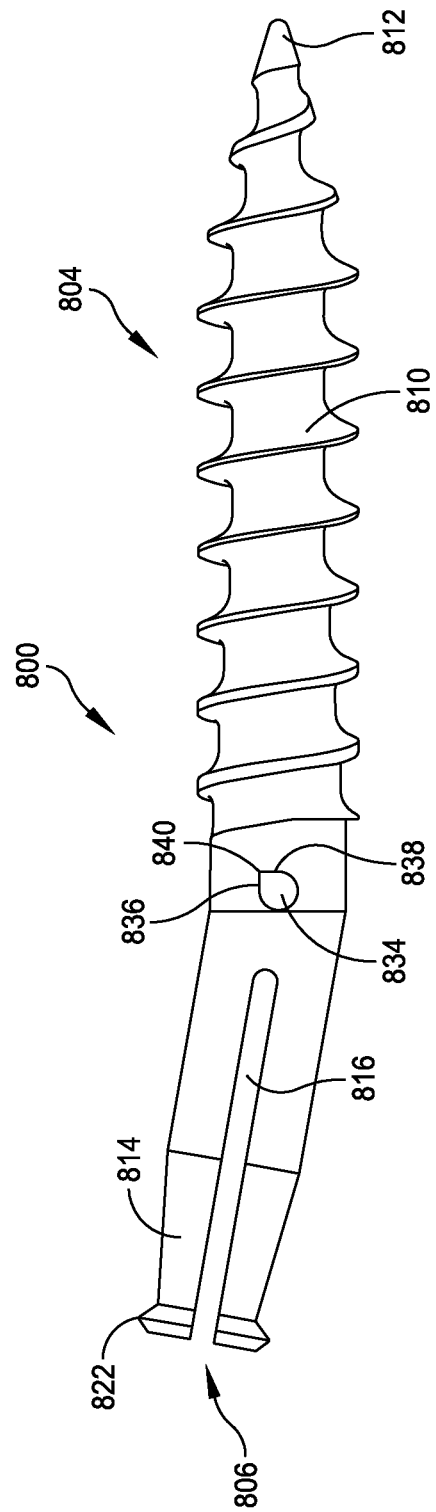
FIG. 31D is a side view of the hammer toe implant illustrated in FIG. 31C.

Although implant 500 is illustrated as having a substantially linear body 502 in FIGS. 22-30B, one skilled in the art will understand that the implant may have an angled body, such as implant 800 illustrated in FIGS. 31A-31D. Like elements of implant 800 have the same reference numerals as the elements of implant 500 increased by 300. As best seen in FIG. 31D, threaded portion 804 and flexible portion 806 of implant 800 extend from engagement portion 808 at angle with respect to each other. In some embodiments, the angle between a central axes defined by threaded portion 804 and flexible portion 806 is between approximately 145° and 180°. In some embodiments, the angle between the central axes defined by threaded portion 804 and flexible portion 806 of implant is between approximately 160° and approximately 175°. In some embodiments, the angle between the central axes defined by threaded portion 804 and flexible portion 806 of implant is between approximately 170°. However, one skilled in the art will understand that other angles are possible.

Figure 27A:
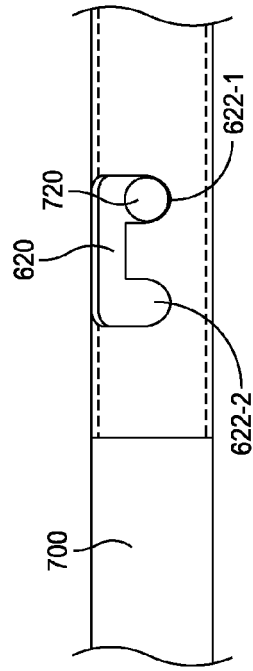
FIG. 27A illustrates the interface between the driving core and the tube illustrated in FIG. 22 at a first stage of implanting the implant.
Figure 27B:
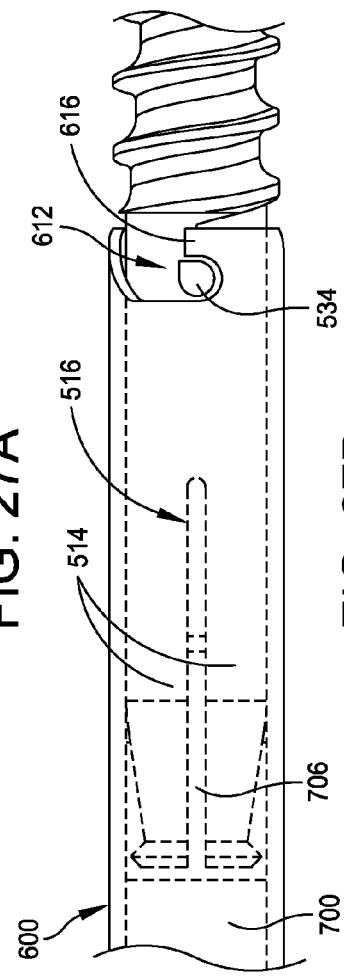
FIGS. 27B and 27C illustrate the interface between the blade of the driving core and the implant disposed within the tube at the first stage of implanting the implant.

The one or more prominences 534, 834 of engagement portion 508, 808 of implants 500, 800 are configured to be engaged by implant engaging end 602 of insertion tube 600 as illustrated in FIGS. 22 and 27B. Turning now to FIG. 24, driving tube 600 has a substantially cylindrical and hollow body 604 and includes a driver core engaging end 606 that defines an opening 608 and is disposed opposite implant engaging end 602, which defines opening 610. Implant engaging end 602 defines a corresponding number of slots 612 as the number of prominences 534 that outwardly extend from implant 500, 800. Slot 612 inwardly extends from implant engaging end 602 and includes a notch 614 that is sized and configured to receive pin 534, 834 therein. Tab 616 of driving tube 600, which defines notch 614, engages flat 538, 838 of pin 534 for preventing relative axial movement between implant 500, 800 and driving tube 600 when prominence 534, 834 is received within notch 614.

Another slot 620 is disposed adjacent to driver core engaging end 606 of driving tube 600. As best seen in FIGS. 24 and 27A, slot 620 extends in a direction that is parallel with respect to a longitudinal axis defined by driving tube 600 and includes a pair of extensions 622-1 and 622-2 (collectively referred to as "extensions 622") that extend in a direction that is substantially orthogonal to the axis defined by driving tube 600. Opening 608 has a diameter that is capable of receiving a portion of driver core 700 therein.

FIGS. 25 and 26 illustrated driver core 700 that includes an elongate body 702 having a first end 704 comprising a fin 706 and a second end 708 comprising a trocar tip or drill tip 710. A first portion 712 of driver core 700 has a cross-sectional diameter that is a smaller than a second portion 714 of driver core 700 to define a ledge or step 716 and such that first portion 712 may be received within driving tube 600. In some embodiments, second portion 712 of driver core 700 has an outer diameter that is approximately equal to an outer diameter of driver core body 702, although one skilled in the art will understand that second portion 714 may have a diameter that is larger or smaller than an outer diameter of driver core 702. Fin 706 has a width such that fin 706 may be received within slots 516, 816 of implant 500, 800 as best seen in FIGS. 27B and 27B. Driver core 700 defines a hole 718 (FIG. 25) along the length of the first portion 712, which is sized and configured to receive a dowel pin 720. In some embodiments, dowel pin 720 is sized to be received within hole 718 in a press fit engagement.

Figure 23B:
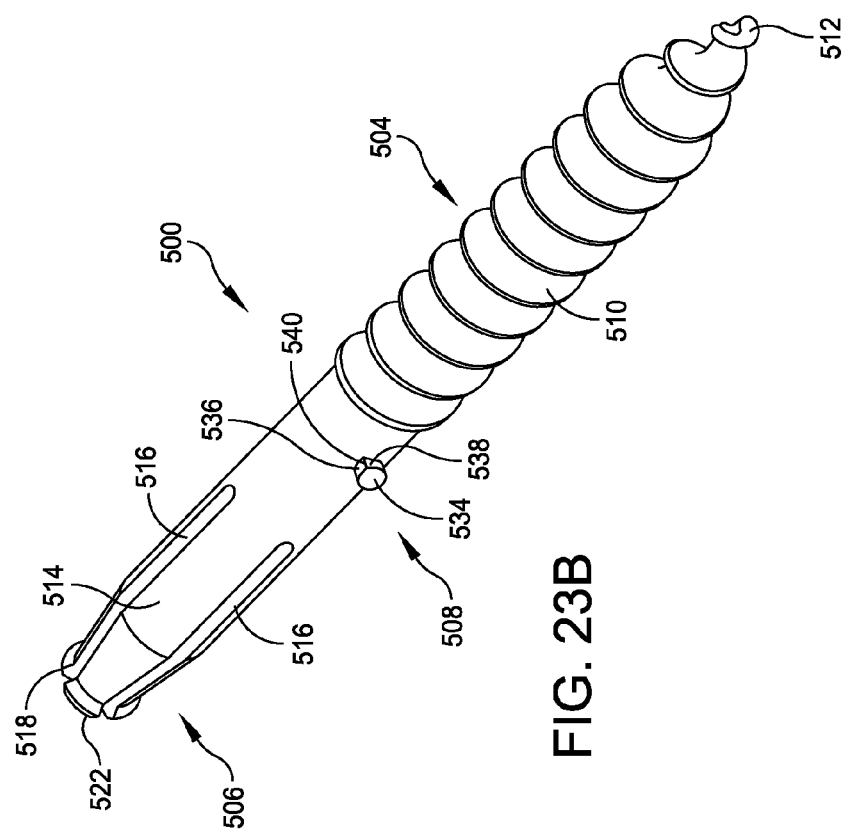
FIG. 23B is an isometric view of the hammer toe implant illustrated in FIG. 23A in its compressed state.
Figure 27C:
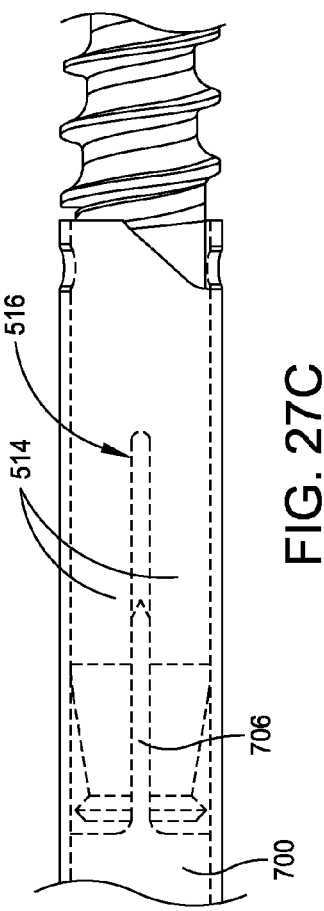

To create the assemblage illustrated in FIG. 22, prongs 514 are compressed from their natural position in which they outwardly extend away from a longitudinal axis defined by implant 500 as illustrated in FIG. 23A to a compressed position as illustrated in FIG. 23B. With prongs 514 compressed, flexible portion 506 of implant 500 is inserted into opening 610 of driving tube 600 (FIGS. 27B and 27C). As flexible portion 506 is inserted into opening 610, prominence 534 is received within slot 612 and within notch 614 by rotating implant 500 with respect to driving tube 600 (FIG. 27B), or vice versa. Implant 800 may be inserted into driving tube 600 in a similar manner except that body 802 of implant 800 is also elastically bent such that body 802 of implant 800 is substantially linear. In order to achieve such elastic deformation, implant 800 may be formed from a superelastic material such as, for example, nitinol or other shape memory alloy.

First portion 712 of driver core 700 is inserted into opening 608 of insertion tube 600. As first portion 712 is received within driving tube 600, fin 706 is aligned with and received within slots 516, 800 of implant 500, 800 disposed at the opposite end of driving tube 600 (FIGS. 27B and 27C). With driver core 700 disposed within insertion tube 600, dowel pin 720 is inserted into hole 718, which is visible through slot 620 and/or one of extensions 622 as shown in FIG. 27A. Dowel pin 720 secures driver core 700 within driving tube 600, but permits relative motion between driver core 700 and driving tube 600 as dowel pin 720 may slide within slot 620 and extensions 622.

With implant 500, driving tube 600, and driver core 700 assembled together, the resultant assemblage may be used to install implant 500 within the joint between the proximal and middle phalanxes via a retrograde approach. For example, access to joint 402 between middle phalanx 404 and proximal phalanx 406 is obtained by making an incision in toe 400. A bone saw or other tool 450 may be used to provide flat surfaces on the ends of middle and proximal phalanxes 404, 406.

Implant engaging end 602 and threaded portion 504, 804 of implant 500, 800 are received within chuck or pin driver 454 of drill 452 such that trocar tip 710 of driver core 700 is exposed and may be driven into proximal surface 410 of middle phalanx 404. As drill 452 rotates in a clockwise direction (or counterclockwise depending on the orientation of extensions 622 and notch 614), dowel pin 720 is received within extension 622-1 and the motion of driving tube 600 is translated to driving core 700. Drill 452 drives driving tube 600 and driving core 700 until trocar tip 710 emerges from the distal tip 412 of distal phalanx 408 such trocar tip 204 extending from distal tip 412 in FIG. 16.

Figure 12:
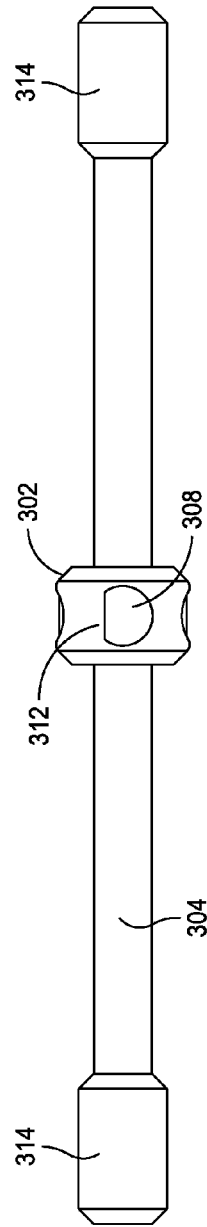
FIG. 12 is a side view of the handle illustrated in FIG. 10.

With trocar tip 710 extending from distal tip 412 of distal phalanx 408, chuck or pin driver 454 is loosened and moved from engaging implant engaging end 602 of driving tube 600 to engaging second portion 714 of driver core 700. The assemblage of implant 500, 800, driving tube 600, and driver core 700 are distally advanced until tip 512 of threaded portion 504, 804 is received within intramedullary channel 414 formed by trocar tip 710. With tip 512 disposed within intramedullary channel 414, middle phalanx 404 and proximal phalanx 406 are aligned with one another, drill 452 is disengaged from driving tube 600 and a driving handle similar to driving handle 300 illustrated in FIGS. 10-12. Specifically, trocar tip 710 and one or more flats 722 are received within an opening defined by the driving handle and engages the one or more flats 722 disposed adjacent to trocar tip 710 on driver core 700.

The physician uses driving handle to rotate and drive implant 500, 800 into proximal phalanx 406 due to the coupling between implant 500, 800, driving tube 600, and driver core 700. The clockwise rotation of threads 510, 810 (or counterclockwise rotation depending the type of threads 510, 810) advances implant 500, 800 into proximal phalanx 406 until implant engaging end 602 of driving tube 600 contacts proximal phalanx 406. In some embodiments, a surgeon may feel when implant engaging end of driving tube 600 contacts the outermost surface of proximal phalanx 406 since the outer diameter of driving tube 600 is greater than an outer diameter of threads 510, 810 of implant 500, 800. To provide a further indication of proper insertion to the surgeon, the minor diameter of threads 510, 810 may increase in diameter such that the surgeon will feel a greater resistance as implant 500, 800 is driven into proximal phalanx 406 and the minor diameter engages the adjacent bone.

Once implant 500, 800 is disposed within proximal phalanx 406, the flexible portion 506, 806 of implant 500, 800 is deployed within distal phalanx 404 by decoupling implant 500, 800 from driving tube 600 and driver core 700. FIGS. 27A-27C illustrate the relative positions of the features of implant 500, 800, driving tube 600, and core 700 prior to decoupling and deployment of implant 500, 800 within proximal phalanx 406. To decouple implant 500, 800 from driving tube 600 and driver core 700, driver core 700 is rotated in an opposite direction (i.e., a counterclockwise direction), which results in dowel pin 720 being disengaged from extension 622-1 and being received within lengthwise slot 620 (FIG. 28A) since driving tube 600 is held in place by virtue of the friction between the outer surface of driving tube 600 and the adjacent bone. The rotation of driver core 700 results in the rotation of implant 500, 800 due to the coupling between fin 706 of driver core 700 and slot 516, 816 defined by implant 500, 800. The rotation of driver core 700 and implant 500, 800 results in only a slight backing out of implant 500, 800 due to the thread pitch of threads 510, 810 being small.

With dowel pin 720 disengaged from extension 622-1, driver core 700 is pulled in an axial direction away from implant 500, 800 causing dowel pin 720 to slide along slot 620 until it contacts wall 624 that defines slot 620 as illustrated in FIG. 29A. The axial movement of driver core 700 relative to tube 600 and implant 500, 800 results in blade 706 being separated from slots 516, 816 of implant 500, 800 as illustrated in FIGS. 29B and 29C since the axial movement of implant 500, 800 is constrained by slot 612 of tube 600.

Driver core 700 is rotated in a clockwise direction such that dowel pin 720 is received within extension 622-2 as illustrated in FIG. 30A. Further clockwise rotation of driver core 700 when dowel pin 700 is disposed within extension 622-2 causes driving tube 600 to rotate in a counterclockwise direction forcing prominence 534 to cam along ramped edge 626 of slot 612 (FIG. 30B) thereby separating implant 500, 800 from its engagement with driving tube 600.

Driver core 700 is pulled axially out of intramedullary channel 414 along with driving tube 600. Once implant engaging end 602 clears end 518, 818 of implant 500, 808, prongs 514, 814 radially flex, such as the flexing of prongs 114 illustrated in FIG. 21, such that an edge 522a of anti-rotational feature 522, 822 engages the adjacent bone of middle phalanx 404. Body 802 of implant 800 will also flex such threaded portion 804 and flexible portion 806 are disposed at an angle with respect to each other.

The retrograde installation technique described above advantageously enables the implant to fuse the DIP or PIP joints with improved alignment of the phalanxes compared to the conventional antegrade techniques. Additionally the implant and implant system disclosed herein do not have the drawbacks as the conventional implants and can be installed via the retrograde technique described above.

Although the systems and methods have been described in terms of exemplary embodiments, they are not limited thereto. Rather, the appended claims should be construed broadly, to include other variants and embodiments of the systems and methods, which may be made by those skilled in the art without departing from the scope and range of equivalents of the systems and methods.

What is claimed is:

1. A method of connecting adjacent bones, comprising:
   forming an incision to gain access to a joint between first and second bones;
   flexing the first and second bones such that the bones are disposed at an angle from one another;
   inserting a pointed tip of a core pin extending from a first end of a tube into a first end of the first bone until a tip of an elongate threaded member of an implant extending from and at least partially disposed within a second end of the tube is received within an intramedullary channel formed by the core pin and tube, the first end of the first bone being closer to the second bone compared to a second end of the first bone;
   repositioning the first and second bones such that they are approximately linearly aligned with each other;
   rotating the core pin in a first direction to drive the elongate threaded member into the second bone;
   decoupling the core pin from its engagement with the implant; and
   withdrawing the core pin and tube from the first bone to disengage the second end of the tube from a flexible portion of the implant including a plurality of prongs,
   wherein the plurality of prongs outwardly flex to contact the first bone when disengaged from the second end of the tube.

2. The method of claim 1, wherein decoupling the core pin from its engagement with the implant includes:
rotating the core pin relative to the tube in a second direction until a pin extending from an outer surface of the core pin is received within a slot defined by the tube, the slot extending in a direction that is approximately parallel to a lengthwise axis defined by the tube; and
moving the core pin along the lengthwise axis relative to the tube such that a fin disposed at an end of the core pin that is opposite an end at which the pointed tip is disposed is moved out of a slot defined by the prongs of the implant.

3. The method of claim 2, wherein the slot defined by the tube includes at least one extension extending in an approximately perpendicular direction to a direction in which the slot extends.

4. The method of claim 2, further comprising:
rotating the core pin and tube in the first direction such that a protrusion outwardly extending from the implant is disengaged with a second slot defined by the tube.

5. The method of claim 4, wherein the second slot defined by the tube is disposed adjacent to the second end of the tube.

6. The method claim 1, wherein the core pin includes at least one flat disposed along its length for being engaged by a tool.

7. The method of claim 1, wherein withdrawing the core pin and tube from the first bone includes:
rotating the core pin and tube in the first direction until a protrusion outwardly extending from the implant is disengaged from a second slot defined by the tube; and
pulling the core pin and tube out of the intramedullary channel.

8. The method of claim 1, wherein a first portion of the core pin that includes the pointed tip has a larger cross-sectional geometry than a second portion of the core pin received within a passageway defined by the tube.

9. The method of claim 8, wherein the second portion of the core pin includes a fin sized and configured to be received within a slot defined by the prongs of the implant.

* * * * *